US006241983B1

(12) United States Patent
Paul et al.

(10) Patent No.: US 6,241,983 B1
(45) Date of Patent: *Jun. 5, 2001

(54) BACTERIA-AND FIBER-CONTAINING COMPOSITION FOR HUMAN GASTROINTESTINAL HEALTH

(75) Inventors: Stephen M. Paul, Rancho Santa Margarita; Jeffrey J. Katke, San Clemente; Kim Carleton Krumhar, Carlsbad, all of CA (US)

(73) Assignee: Metagenics, Inc., San Clemente, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/320,429

(22) Filed: May 26, 1999

Related U.S. Application Data

(63) Continuation-in-part of application No. 09/062,204, filed on Apr. 17, 1998, which is a continuation of application No. 08/674,115, filed on Jul. 1, 1996, now Pat. No. 5,744,134, which is a continuation of application No. 08/437,316, filed on May 9, 1995, now Pat. No. 5,531,989, which is a continuation-in-part of application No. 08/331,140, filed on Oct. 28, 1994, now Pat. No. 5,531,988.

(51) Int. Cl.$^7$ ............................. A61K 9/50; A61K 39/395
(52) U.S. Cl. .......................................................... 424/93.4
(58) Field of Search .................................. 424/405, 93.4, 424/93.45, 161.1, 195.1, 234.1, 246.1, 499, 500, 809

(56) References Cited

U.S. PATENT DOCUMENTS

| | | |
|---|---|---|
| 4,091,117 | 5/1978 | Mutai et al. . |
| 4,377,569 | 3/1983 | Plymate . |
| 4,512,977 | 4/1985 | Lundy . |
| 4,784,852 | 11/1988 | Johannson . |
| 4,806,368 | 2/1989 | Reddy . |
| 4,816,252 | 3/1989 | Stott et al. . |
| 4,834,974 | 5/1989 | Stott et al. . |
| 4,977,137 | 12/1990 | Nichols et al. . |
| 4,994,442 | 2/1991 | Gil et al. . |
| 5,066,491 | 11/1991 | Stott et al. . |
| 5,145,698 | 9/1992 | Cajigas . |
| 5,240,909 | 8/1993 | Nitsche . |
| 5,330,756 | 7/1994 | Stewart et al. . |
| 5,413,765 | 5/1995 | Nanji . |
| 5,456,924 | 10/1995 | Bounous et al. . |
| 5,531,988 | 7/1996 | Paul . |
| 5,531,989 | 7/1996 | Paul . |
| 5,645,834 | 7/1997 | Corkrum . |
| 5,744,134 | 4/1998 | Paul . |
| 5,785,990 | 7/1998 | Langrehr . |
| 5,795,602 | 8/1998 | Craig et al. . |
| 5,846,569 | 12/1998 | Anderson et al. . |

FOREIGN PATENT DOCUMENTS

WO 99-64022  6/1998  (WO) .

OTHER PUBLICATIONS

Spectra Plex™ and Acidophilus Over Candida and Saimonella (consisting of 2 pages).
S. Tzipori, et al.; Remission of Diarrhoea Due to Cryptosporidiosis in an Immunodeficient Child Treated With Hyperimmune Bovine Colostrum; 1276–1277; 1986; British Medical Journal vol. 293.
E. B. Collins, et al.; Growth of Bifidobacteria in Milk and Preparation of Bifidobacterium Infantis for a Dietary Adjunct; 1376–1380; 1984; Journal of Dairy Science vol. 67.
N. Trenev, et al.; The Role of Probiotics in Geriatric and Infant Nutrition; 746–747; 1994; Townsend Letter for Doctors.
Bifadobacterium Adolescentis as Best Probiotic Selection; 1–8; 1992; Nutritional Consultants Group, Inc.
Advertisement "Intestinal Fortitude" Probioplex™ Metagenics, Genetic Potential Through Nutrition (consisting of 2 pages).
Robert H. Yolken, et al.; Antibody to Human Rotavirus in Cow's Milk; 605–610; 1985; The New England Journal of Medicine vol. 312, No. 10.
Harold Brussow, et al.; Bovine Milk Immunoglobulins for Passive Immunity to Infantile Rotavirus Gastroenteritis; 982–986; 1987; Journal of Clinical Microbiology.
Helmut Hilper, et al; Use of Bovine Milk Concentrate Containing Antibody to Rotavirus to Treat Rotavirus Gastroenteritis in Infants; 158–166; 1987; The Journal of Infectious Diseases, vol. 156, No. 1.
Gustavo Boutlous, et al.; The Immunoenhancing Property of Dietary Whey Protein Concentrate; 271–278; No. 11, No. 4.
Carol O. Tacket, et al.; Protection by Milk Immunoglobulin Concentrate Against Oral Challenge with Enterotoxigenic *Escherichila Coli*; 1240–1243; 1988; The New England Journal of Medicine; vol. 318, No. 19.
O. deRham, et al.; Proteolysis of Bovine Immunoglobulins; 62–67, 69; 1977; Int. Arcs Allergy App. Immun, 55.
Masashi Sato, et al.; Estimation of Circulating Immune Complexes Following Oral Challenge with Cow's Milk in Patients with IgA Nephropathy; 43–48; 1987; Nephron 47.

(List continued on next page.)

*Primary Examiner*—Raymond Henley, III
(74) *Attorney, Agent, or Firm*—Clayton, Howarth & Cannon, P.C.

(57) ABSTRACT

A composition for promoting gastrointestinal health contains an effective amount of a beneficial human intestinal microorganism and an effective amount of dietary fiber. Preferably, the dietary fiber is a member selected from the group consisting of pentosans, β-glucans, pectins and pectic polysaccharides, mannans, arabinans and galactans, fructo-oligosaccharides, and mixtures thereof. The bacteria- and fiber-containing composition can optionally contain one or more of an immunoglobulin composition containing concentrated immunologically active immunoglobulins, components of a non-immune defense system, an iron-sequestering molecule, and gluconic acid. Preferred beneficial human intestinal microorganisms include lactobacilli and bifidobacteria. Methods of use are also described.

60 Claims, No Drawings

OTHER PUBLICATIONS

C. Cunningham–Rundles, et al; Dietary Bovine Antigens and Immune Complex Formation After Intravenous Immunoglobulin in Common Varied Immunodeficiency; 381–388; 1986; Journal of Clinical Immunology; vol. 6, No. 5.

C. Mietens, et al.; Treatment of Infantile *E. coli* Gastroenteritis with Specific Bovine anti–*E coli* Milk Immunoglobulines; 239–252; 1979, European Journal of Pediatrics, 132.

Thomas E. Besser, et al; Passive Immunity to Bovine Ratavirus Infection Associated with Transfer of Serum Antibody into the Intestinal Lumen; 2238–2243; 1988; Journal of Virology, vol. 62, No. 7.

Joseph C. Kolars, M.D. et al; Yogurt–an Autodigesting Source of Lacrose; 1–3; 1984; The New England Journal of Medicine; vol. 310, No. 1.

Marie–Hélène Coconnier, et al.; Protein–Mediated Adhesion of Lactobacillus Acidophilus BG2F04 on Human Enterocoyte and Mucus–Secreting Cell Lines in Culture; 2034–2039; 1992; Applied and Environmental Microbiology, vol. 58, No. 6.

S.E. Gilliland, et al.; Factors to Consider when Selecting a Culture of Lactobacillus acidophilus as a Dietary Adjunct to Produce a Hypocholesterollemic Effect in Humans; 905–911; 1990, Journal of Dairy Science, vol. 73, No. 4.

L. Alm, The Effect of Lactobacillus Acidophilus Administration Upon the Survival of Salmonella in Randomly Selected Human Carriers; 13, 1983, Prog. Fd. Nurr. Sci., vol. 7.

S.E. Gilliland, et al.; Antagonistic Action of Lactobacillus acidophilus Toward Intestinal and Foodbone Pathogens in Associative Cultures; 820; 1977; Journal of Food Protection, vol. 40, No. 12.

Viki L. Hughes, MT, et al.; Microbiologic Characteristics of Lactobacillus Products Used for Colonization of the Vagina; 244, 246, 248; Obstetrics & Gynecology.

Eileen Hilton, M.D., et al.; Ingestion of Yogurt Containing Lactobacillus acidophilus as prophylaxis for Candidal Vaginitis; 353–357; 1992; American College of Physicians, vol. 116, No. 5.

E. Collins, et al.; Inhibition of Candida Albicans by Lactobacillus acidophilus; 830–832; 1980; Journal of Dairy Science, vol. 63, No. 5.

E.G. Kleeman, et al.; Adherence of Lactobacillus Species to Human Fetal Intestinal Cells; 2063–2069; 1982; Journal of Dairy Science, vol. 65, No. 11.

V. Herbert, et al.; Contribution of the Microflora of the Small Intestine to the Vitamin B12 Nutriture of Man; 274–275; 1980, Nutrition Review, vol. 38, No. 8.

Clark Beck, M.D. et al.; Beneficial Effects of Administration of Lactobacillus Acidophilus in Diarrheal and other Intestinal Disorders; 522–530; 1961; The American Journal of Gastroenterology, vol. 35.

Alexander G .Schauss; Lactobacillus Acidophilu: Method of Action, Clinical Application, and Toxeity Data; 1–12; 1990; Journal of Advancement in Medicine (In Press).

Jerzy Meduski, M.D., Ph.D.; Latobacillus acidophilus Synopsis of its Attributes (consisting of 2 pages).

Ron Kohen, et al; Prevention of Oxidative Damage in the Rat Jejunal Mucosa by Pectin, *British J. of Nutrition*; 69, pp. 789–800, 1993.

Flourie B. et al; The effect of Pectin on Jejunal glucose absorption and unstirred layer thickness in normal man. *GUY*, 1984, Sep. 25(9) pp. 1936–1941.

Arbman, Gunnar MD, Cereal Fiber, Calcium and Colorectal Cancer, *Cancer*, vol. 69, No. 8, pp. 2042–2048, Apr. 15, 1992.

Jenkins, David et al; Dietary Fiber, Fiber Analogues and Glucose Tolerance, Importance of Viscosity; *British Medical Journal* 1, 1392–1394, May 27, 1978.

Sato H, et al; Antioxidant Activity of Synovial Fluid, Hyaluronic Acid, and Two subcomponents of Hyaluronic Acid, *Arthritis And Rheumatism*, vol. 31, No. 1, Jan. 1988.

Reiter, B; Bacterial Inhibitors in Milk and other Secretions, with Special Reference to the Complement, Transferrin/Lactoferrin and Lactoperoxidase/Thiocyanate/Hydrogen Peroxide Systems. Inhibition and Inactivation of Vegetative Microbes, Academic Press, pp. 31–60, 1976.

Reiter, Bruno and Perraudin, J–P; Lactoperoxidase: Biological Functions: In Peroxidases in Chemistry and Biology, CRC Press, vol. #1, pp. 143–180, 1991.

Probioplex: Intestinal Fortitude, "sell sheet" published by Metagenics, Inc. (Jun. 1989).

BACTERIA-AND FIBER-CONTAINING COMPOSITION FOR HUMAN GASTROINTESTINAL HEALTH

CROSS-REFERENCE TO RELATED APPLICATIONS

This application is a continuation-in-part of application Ser. No.09/062,204, filed Apr. 17, 1998, which is a continuation of application Ser. No. 08/674,115, filed Jul. 1, 1996, now U.S. Pat. No. 5,744,134, which is a continuation of application Ser. No. 08/437,316, filed May 9, 1995, now U.S. Pat. No. 5,531,989, which is a continuation-in-part part of application Ser. No. 08/331,140, filed Oct. 28, 1994, now U.S. Pat. No. 5,531,988.

BACKGROUND OF THE INVENTION

This invention relates to a bacteria- and fiber-containing composition and methods of use thereof for promoting gastrointestinal health. More particularly, the invention relates to a composition comprising living bacteria that are beneficial for gastrointestinal health; soluble and insoluble dietary fiber that provides the advantages typically offered by dietary fibers with the additional advantages of not affecting blood glucose or insulin levels, being readily fermented by the intestinal microflora, and promoting growth of certain beneficial intestinal microorganisms; and optionally one or more of the following: concentrated immunoglobulins capable of binding and inactivating foreign antigens such as pathogenic bacteria, viruses, fungi, and protozoa that are detrimental to gastrointestinal health, lactoperoxidase and/or thiocyanate for strengthening a natural non-immune defense system, lactoferrin for inhibiting detrimental iron-catalyzed processes and harmful microorganisms, and gluconic acid for inhibiting growth of harmful bacteria and stimulating immune function.

Fiber in the diet is well known for its salutary effects on gastrointestinal health. Such effects include providing bulk to the stool, decreasing the pH of the gastrointestinal tract, producing volatile fatty acids, decreasing intestinal transit time, and beneficially influencing various blood parameters. Dietary fiber has also been shown to have a beneficial effect on cholesterol and lipid metabolism that results in decreased serum cholesterol, triglycerides, and phospholipids and an improved (increased) HDL to LDL ratio. A study on laboratory animals showed that adding fiber to the diet decreases the incidence of bacterial translocation, i.e. crossing the intestinal barrier and entering systemic circulation. C. Palacio et al., Dietary Fiber: Physiologic Effects and Potential Applications to Enteral Nutrition, in Clinical Nutrition: Enteral and Tube Feeding (2d. ed., 1990). Nutritional and epidemiological studies have indicated that a general increase in the consumption of dietary fiber may play a role in preventing deleterious effects of oxygen free radicals that have been accused of being involved in such processes as aging, inflammation, and some disease processes. R. Kohen et al., Prevention of Oxidative Damage in the Rat Jejunal Mucosa by Pectin, 69 Br. J. Nutrition 789 (1993).

Certain bacteria have also been shown to be beneficial to human gastrointestinal health. Bacteria of the genus Lactobacillus have been used for several hundred years for treating various illnesses. Lactobacilli found in the human intestinal tract include *L. acidophilus, L. casei, L. fermentum, L. salivaroes, L. brevis, L. leichmannii, L. plantarum,* and *L. cellobiosus.* In recent years, *L. acidophilus* has been shown to be exceptionally useful in treating conditions such as antibiotic-induced imbalances in the gastrointestinal microflora, hypercholesterolemia, vaginal infections, *E. coli* infection, oral contraceptive failure, depressed immunity, cancerous tumors, chronic granulomatous disease, and lactose indigestion. A. G. Shauss, Method of Action, Clinical Application, and Toxicity Data, 3 J. Advancement Med. 163 (1990). In vitro studies have shown *L. acidophilus* to have an inhibitory effect on the growth of pathogenic bacteria such as *Campylobacter pylori, Staphylococcus aureus, Pseudomonas aeruginosa,* and *Sarcina lutea* K. M. Shahani et al., Natural Antibiotic Activity of Lactobacillus Acidophilus and Bulgaricus, 11 Cultured Dairy Products J. 14 (1976).

The beneficial effect of *L. acidophilus* is further illustrated by preliminary evidence that *L. acidophilus* inhibits the toxic activities of bacteria in patients with chronic kidney failure. M. L. Simenhoff et al., Biomodulation of Uremic Pathophysiology in Man, abstract presented at Am. Soc. of Nephrology Meeting, Baltimore, 1992. Such patients often have toxic levels of amines in their blood due to bacterial overgrowth in the small bowel. Consumption of high levels of freeze dried bacteria drastically reduced levels of these toxic amines. These results demonstrate the ability of *L. acidophilus* to exert a positive effect on the microflora of the intestines.

It has also been shown that the activities of fecal bacterial enzymes thought to play a role in conversion of procarcinogens to carcinogens, such as beta-glucuronidase, nitroreductase, and azoreductase, were reduced 2- to 4-fold in subjects taking *L. acidophilus* supplements. B. R. Goldin & L. S. Gorbach, The Effect of Milk and Lactobacillus Feeding on Human Intestinal Bacterial Enzyme Activity, 39 Amer. J. Clin. Nutr. 756 (1984). These results suggest that dietary supplementation with *L. acidophilus* may reduce the risk of developing colon cancer.

Bifidobacteria are also known to exert a beneficial influence on human health. These bacteria exert antimicrobial activity in the human intestine by producing lactic acid and acetic acid as a result of carbohydrate metabolism. These acids lower the intestinal pH, thereby inhibiting overgrowth of gastrointestinal pathogens. Therapeutic applications of bifidobacteria are indicated for the management of diarrhea and constipation, and the management of hepatic encephalopathy with hyperammonemia. Additional benefits include the production of B vitamins and breakdown of carcinogenic N-nitrosamines.

*Bifidobacterium adolescentis* is the predominant species of bacteria in humans after age two. This predominance suggests its exceptional stability and prolonged proliferation in the intestine. Nevertheless, for any preparation of living microorganisms to function as a commercial dietary supplement, in addition to being able to provide a beneficial effect must also exhibit good survival in storage, resistance to inactivation by bile, and survival through the gastrointestinal tract. Strain-to-strain or isolate-to-isolate variability can occur as to these traits, thus the selected properties should be verified before commercializing any particular product containing such microorganisms.

While prior art formulas as dietary supplements containing soluble dietary fiber or beneficial bacteria are known and are generally suitable for their limited purposes, they possess certain inherent deficiencies that detract from their overall utility in restoring and maintaining gastrointestinal health. For example, a dietary supplement containing dietary fiber without living intestinal bacteria that are beneficial for gastrointestinal health lack means for providing an inhibitory effect on the growth of pathogenic bacteria, reducing levels of toxic amines, and lowering the pH of the gastrointestinal tract. Similarly, a dietary supplement containing beneficial bacteria without dietary fiber lacks means for providing bulk to the stool, decreasing the pH of the gastrointestinal tract, producing volatile fatty acids, decreasing intestinal transit time, beneficially influencing various blood parameters, beneficially influencing cholesterol and lipid metabolism, decreasing the incidence of bacterial translocation, preventing deleterious effects of oxygen free radicals, and favoring the growth of beneficial bacteria in the gastrointestinal tract. Further, prior art formulas that fail to include concentrated immunoglobulins lack means for binding and inactivating foreign antigens such as pathogenic bacteria, viruses, fungi, and protozoa that can infect the gastrointestinal tract and are detrimental to the health thereof. Further, prior art dietary supplements fail to provide components, such as lactoperoxidase and thiocyanate, that strengthen the body's natural non-immune defense system or LP-system. Moreover, these formulas do not contain inhibitors of detrimental iron-catalyzed processes and stimulators of immune function.

In view of the foregoing, it will be appreciated that a composition for improving and maintaining gastrointestinal health comprising a beneficial human intestinal microorganism and dietary fiber that provides the typical advantages of a dietary fiber and additionally is low in calories, does not affect blood glucose or insulin levels, and favors the growth of beneficial bacteria in the gastrointestinal tract, while at the same time inhibiting the growth of potentially pathogenic or harmful microorganisms would be a significant advancement in the art. It will also be appreciated that a composition for improving and maintaining gastrointestinal health comprising an immunoglobulin preparation containing immunoglobulins that bind and inactivate pathogenic microorganisms in the gastrointestinal tract would be another significant advancement in the art.

BRIEF SUMMARY OF THE INVENTION

It is an object of the present invention to provide a composition for use as a dietary supplement that benefits human gastrointestinal health when administered orally.

It is also an object of the invention to provide a composition for use as a dietary supplement that, when ingested, is effective for treating ailments due to gastrointestinal pathogens such as bacteria, viruses, fungi, or protozoa.

It is another object of the invention to provide a composition for use as a dietary supplement that, when ingested, results in decreased serum cholesterol, triglycerides, and phospholipids and an increased HDL to LDL ratio.

It is still another object of the invention to provide a composition for use as a dietary supplement that aids in preventing deleterious effects of oxygen free radicals.

It is yet another object of the invention to provide a composition for use as a dietary supplement that bolsters the body's immune system and the natural non-immune system, i.e. the LP system.

It is a further object of the invention to provide a composition for use as a dietary supplement that inhibits detrimental iron-catalyzed processes in the body.

These and other objects can be addressed by providing a bacteria- and fiber-containing composition for use as a dietary supplement for restoring and maintaining gastrointestinal health comprising:

(a) an effective amount of beneficial human intestinal microorganisms; and (b) an effective amount of dietary fiber. The dietary fiber can be any soluble dietary fiber or some insoluble fibers that have a favorable influence on the growth of certain bacteria. Preferably, the dietary fiber is a member selected from the group consisting of fructo-oligosaccharides, such as inulin, soy fructo-oligosaccharides, and banana fiber; pectins and pectic polysaccharides; mannans, such as guar gum, locust bean gum, konjac, and xanthan gum; pentosans, beta-glucans, arabinans and galactans, such as larch arabinogalactans; and mixtures thereof. In a more preferred embodiment of the invention, the composition comprises in percent by weight (a) about 0.1% to about 20% of the beneficial human intestinal microorganisms; and (b) about 40% to about 60% of the dietary fiber. The beneficial human intestinal microorganisms are most preferably present in an amount in the range of about 5% to about 10% by weight. The beneficial human intestinal microorganisms are preferably selected from the group consisting of lactobacilli and bifidobacteria. More preferably, the beneficial human intestinal microorganisms are selected from the group consisting of *Lactobacillus acidophilus, L. bulgaricus, L. casei, L. fermentum, L. salivaroes, L. brevis, L. leichmannii, L. plantarum, L. cellobiosus, Bifidobacterium adolescentis, B. infantis, B. longum, B. thermophilum,* and *B. bifidum.* Most preferably, the beneficial human intestinal microorganisms are selected from *L. acidophilus* and *B. adolescentis.* A preferred strain of *L. acidophilus* is strain NCFM. The bacteria- and fiber-containing composition can also optionally contain one or more of the following ingredients:

| | Ranges in Percent by Weight | |
|---|---|---|
| Ingredient | Broad | Preferred |
| Lactoperoxidase | 0–0.0300% | 0.0001–0.0300% |
| Thiocyanate salt | 0–0.0500% | 0.0001–0.0500% |
| Lactoferrin | 0–0.1000% | 0.0001–0.1000% |
| Gluconic acid | 0–10% | 0.1–10% |

The bacteria- and fiber-containing composition can also optionally contain an effective amount of an immunoglobulin composition comprising concentrated immunologically active immunoglobulins. In preferred amounts, the immunoglobulin composition is present in amounts ranging from about 40% to about 60% by weight. The immunoglobulin composition can include a carrier. A preferred carrier comprises at least one member selected from the group consisting of a carbohydrate and a lipid, wherein the carbohydrate is capable of being an energy source for a beneficial human intestinal microorganism and the lipid aids in reconstitution of the immunoglobulin composition. A preferred carbohydrate is maltodextrin, and a preferred lipid is lecithin. Preferably, the immunoglobulin composition is purified from a source selected from the group consisting of milk, milk products, and whey, with a bovine source also being preferred.

A method of restoring and maintaining gastrointestinal health comprises the step of orally administering an effective amount of a bacteria- and fiber-containing composition for promoting gastrointestinal health comprising:

(a) an effective amount of beneficial human intestinal microorganisms; and (b) an effective amount of dietary fiber.

DETAILED DESCRIPTION

Before the present composition and methods of use are disclosed and described, it is to be understood that this invention is not limited to the particular examples, process steps, and materials disclosed herein as such process steps and materials may vary somewhat. It is also to be understood that the terminology used herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise. Thus, for example, reference to a composition containing "a microorganism" includes a mixture of two or more microorganisms, reference to "an immunoglobulin" includes reference to two or more of such immunoglobulins, and reference to "a concentrate" includes reference to a mixture of two or more of such concentrates.

In describing and claiming the present invention, the following terminology will be used in accordance with the definitions set out below.

As used herein, "beneficial human intestinal microorganism" means an organism of microscopic size, such as a bacterium, that inhabits the human intestine and exerts a beneficial effect on the gastrointestinal health of an individual in which it resides. Preferred beneficial human intestinal microorganisms according to the present invention include bacteria of the genera Lactobacillus and Bifidobacterium. A more preferred lactobacillus is *L. acidophilus*, with *L. acidophilus* strain NCFM being most preferred, and a more preferred bifidobacterium is *B. adolescentis*. Other lactobacilli that are beneficial to gastrointestinal health include *L. bulgaricus, L. casei, L. fermentum, L. salivaroes, L. brevis, L. leichmannii, L. plantarum,* and *L. cellobiosus*. Other bifidobacteria that are beneficial to gastrointestinal health include *B. infantis, B. longum, B. thermophilum,* and *B. bifidum*.

As used herein, "dietary fiber" and similar terms mean fiber that is suitable for human consumption. Such dietary fiber can be any soluble dietary fiber or certain insoluble dietary fibers that have a favorable influence on the growth of certain beneficial intestinal bacteria.

As used herein, "soluble dietary fiber" and similar terms mean fiber that is water soluble and suitable for human consumption. Soluble dietary fiber should provide known salutary effects on gastrointestinal health such as providing bulk, decreasing pH of the gastrointestinal tract, producing volatile fatty acids, decreasing intestinal transit time, beneficially influencing various blood parameters, having a beneficial effect on cholesterol and lipid metabolism, decreasing the incidence of bacterial translocation, and preventing the deleterious effects of oxygen free radicals, such as have been reviewed above.

As used herein, "insoluble dietary fiber" and similar terms mean fiber that is insoluble in water, suitable for human consumption, and provides the beneficial effect of favorably influencing the growth of certain beneficial intestinal bacteria.

As used herein, "immunoglobulin composition" means a composition comprising an effective amount of immunologically active immunoglobulins. Preferably, these are present as concentrated immunologically active immunoglobulins. One such immunoglobulin composition is sold under the trademark "PROBIOPLEX" by Metagenics, Inc. (San Clemente, Calif.). PROBIOPLEX contains (1) about 55–60 parts by weight of an immunoglobulin concentrate from bovine whey wherein at least about 7% by weight of the total solids in the concentrate is immunologically active immunoglobulins, (2) about 35–40 parts by weight of a mixture of carbohydrates including rice maltodextrin and lactose, and (3) about 5–10 parts by weight of lipid including lecithin. Thus, at least about 3.6% by weight of the total PROBIOPLEX composition comprises immunologically active immunoglobulins. The carbohydrates and lipids function as inert carriers for the immunoglobulins. The rice maltodextrin can function further as an energy source for beneficial microorganisms with which the immunoglobulin composition can be mixed in accordance with the present invention. The lecithin aids in dispersion of the powder form of the immunoglobulin composition when reconstituted with water or other liquid. Although PROBIOPLEX contains ingredients other than concentrated immunologically active immunoglobulins, these other ingredients are optional components of the invention. What is required is that the immunoglobulin composition contain an "effective amount" of immunologically active immunoglobulins that are preferably present in concentrated form.

As used herein, "immunologically active" and similar terms mean that the immunoglobulins are active in binding antigens.

As used herein, "effective amount" means an amount necessary to achieve a selected result. For example, an effective amount of a bacteria- and fiber-containing composition useful for reducing the titer of a selected pathogenic microorganism in the gastrointestinal tract would be an amount that achieves the selected result of reducing the titer of the microorganism. Such an amount can be readily determined without undue experimentation by a person of ordinary skill in the art.

As used herein, "thiocyanate salt" means a nutritionally acceptable salt of the thiocyanate anion, such as sodium thiocyanate, potassium thiocyanate, ammonium thiocyanate, and mixtures thereof.

As used herein, "nutritionally acceptable" means generally regarded as safe for human consumption.

Fructo-oligosaccharides (FOS) are long-chain polysaccharides comprised primarily of fructose monosaccharides bonded together by 1-β-D-fructofuranosyl linkages. They are considered indigestible in the human gut. They are metabolized, however, by gut flora including *Lactobacillus acidophilus* and *Bifidobacterium infantis,* resulting in increased numbers of beneficial bacteria, lower gut pH, inhibition of pathogens, and other significant health results. Illustrative fructo-oligosaccharides include inulin, banana fiber, and soy fructo-oligosaccharides. Fructo-oligosaccharides are widely distributed in nature and are found in honey, beer, onion, asparagus, Chinese chive, banana, maple sugar, oats, and Jerusalem artichoke.

Inulin is a storage carbohydrate found in many plants including onion, asparagus, artichoke, and many cereals. Chicory root and Jerusalem artichoke each contain about 70% by weight of inulin. Inulin has been an important food in Europe for many years and is currently being used as a source of dietary fiber, for replacing fat in the diet, and for promoting growth of beneficial bacteria in the intestine. In the U.S., inulin is added to all types of noodles. It has a moderately sweet taste, is highly soluble, and is a frequent replacement for sugar in many foods. Medically, inulin is the substance of choice to study renal clearance and impaired kidney function.

Upon ingestion, both fructo-oligosaccharides are hydrolyzed to a negligible extent as they pass through the mouth, stomach, and small intestine. In the large intestine, they are readily fermented by the intestinal microflora. These carbohydrates are metabolized by the bacteria into short chain fatty acids, mainly acetic, propionic, butyric, and lactic acids. As a consequence of this fermentation, a considerable amount of bacterial mass is produced, which increases stool wet weight. The short chain fatty acids are absorbed by the large intestine and are further metabolized in the liver. This allows the body to recover some energy from FOS, although the efficiency of energy conversion is markedly lower than with other carbohydrates. This phenomenon underlies the low calorie content of fructans and dietary fibers.

FOS is used as a source of energy in the intestinal tract mainly by bacteria in the genus Bifidobacterium. H. Hidaka et al., Effects of Fructooligosaccharides on Intestinal Flora and Human Health, 5 Bifidobacteria Microflora 37–50 (1986). When FOS is administered in the diet, the bifidobacteria increase significantly, becoming the predominant bacteria in the intestinal population, and the clostridia, which are a measure of potentially pathogenic microorganisms, are significantly reduced. As will be discussed in more detail below, bifidobacteria are human intestinal bacteria that provide beneficial effects on gastrointestinal health. Other important groups of bacteria in the mixed population in the intestines, such as Fusobacterium, Lactobacillus, and aerobic bacteria, are not significantly affected by the administration of FOS. H. Hidaka et al., Effects of Fructooligosaccharides on Intestinal Flora and Human Health, 5 Bifidobacteria Microflora 37–50 (1986).

It has been shown, A. Hata, The Influence of Neosugar on the Lipid Metabolism of Experimental Animals, Proc. 1st Neosugar Res. Conference, Tokyo (1982), that fructo-oligosaccharides in the diet of experimental animals cause reduction of blood sugar, serum cholesterol, triglycerides, and phospholipids; significant improvement in the HDL/LDL ratio; an increase in free fatty acids; and significant decreases in total cholesterol in lipedemia cases.

It has also been shown, H. Hadaka et al., Effects of Fructooligosaccharides on Intestinal Flora and Human Health, 5 Bifidobacteria Microflora 37–50 (1986), that administration of fructo-oligosaccharides enhances growth of the bifidobacteria population in the intestine, suppresses production of putrefactive factors, improves blood lipid levels in hyperlipidemia patients, and provides relief from constipation.

Therefore, at least the following positive effects are obtained by addition of fructo-oligosaccharides (FOS) to a composition for use as a dietary supplement according to the present invention: reduction of intestinal disorders, enhancement of a balanced intestinal microflora, and remediation of constipation.

Another preferred dietary fiber according to the present invention is the pectins and pectic polysaccharides (high and low methoxyl pectins). Pectin is a highly water soluble, noncellulosic polysaccharide fiber that occurs naturally as a partial methyl ester of α-(1→4) linked D-polygalacturonate sequences interrupted with (1→2)-L-rhamnose residues. The term pectic polysaccharides refers to galacturonans or, more commonly, rhamno-galacturonans wherein (1-4)-α-D-galacturonan chains are interrupted at intervals by insertion of (1-2)-α-L-rhamnose residues. Other constituent sugars attached as side chains include D-galactose, L-arabinose, D-xylose, and, less frequently, L-fucose and D-glucuronic acid. Most of these sugars occur in short side chains, although D-galactose and L-arabinose are often found in multiple units. Extremely complicated side chains containing neutral pectic polymers such as galactans and arabinans, xyloglucans, and galactomannans have been reported. The molecular weight of the pectins has been reported to range from 30,000 to 300,000.

Pectin is extracted from the primary cell walls of plants. Rich sources of pectin include lemon and orange rinds, which contain about 30% by weight of this polysaccharide. Pectins are used as gelling and thickening agents in food technology and as an antidiarrheal in veterinary medicine.

Another dietary fiber that can be used advantageously in the present invention is the mannans, such as guar gum, locust bean gum, konjac, ad xanthan gum. In some plant cell walls, glucomannans and galactomannans may be present as the major non-cellulosic hexosans. The glucomannans are comprised of (1-4)-β-linked glucose and mannose units, while the galactomannans are comprised of a (1-4)-β-mannan backbone substituted with single units of (1-6)-α-galactose. While no evidence has been reported for the occurrence of galactomannans in cereal grains, all endospermic legumes, such as guar and locust bean contain galactomannans in the endosperm during seed development. Glucomannans have been found as a minor component of cereal grains.

Guar gum is produced from the ground endosperms of *Cyamopsis tetragonolobus,* a legume cultivated in India as a livestock feed. The water soluble fraction, which comprises about 85% of guar gum and is known as guaran, consists of linear chains of (1→4)-β-D-mannopyranosyl units with α-D-galactopyranosyl units attached by (1→6) linkages. The ratio of D-galactose to D-mannose is 1:2. Guar gum has 5 to 8 times the thickening power of starch and, thus, is used as a thickener in foods, as a binder and disintegrating agent in tablet formulations, and in pharmaceuticals and cosmetics.

Pectins and mannans have several beneficial effects on the gastrointestinal tract, such as maintaining the morphology of intestinal villi, increasing lipase activity in the small bowel, delaying gastric emptying time, increasing intestinal transit time, and promoting increased fecal production of short chain fatty acids. It is believed that pectins and mannans in the diet lower blood glucose and serum cholesterol levels, B. Flourie et al., The Effect of Pectin on Jejunal Glucose Absorption and Unstirred Layer Thickness in Normal Man, 25 Gut 1936 (1984). Also, dietary fiber supplementation with pectins or mannans has also been found to significantly suppress the incidence of colon cancer. G. Arbman, Cereal Fiber, Calcium and Colorectal Cancer, 69 Cancer 2042 (1992). Studies with whole apples show that fiber (pectin) in the fruit reduces the insulin response to the sugar in the fruit and prevents "rebound" hypoglycemia. D. Jenkins et al., Dietary Fiber, Fiber Analogues and Glucose Tolerance, Importance of Viscosity, 1 Br. Med. J. 1392 (1978). Further, pectins and mannans are readily degraded by bacterial fermentation in the colon, probably because of their high water solubility.

Moreover, pectins and mannans are also thought to prevent oxidative damage in the gastrointestinal tract. Oxygen free radicals are involved in many deleterious processes including aging, inflammation, and some disease processes. The gastrointestinal mucosa is exposed to oxidants produced within the lumen and in the epithelial cells. Potential sources of luminal oxidants include ingested food, catalase-negative bacteria, and cigarette smoke and other pollutants. The production of reactive free radicals during metabolism of dietary fat can explain some the biological damage such as loss of membrane function, inactivation of membrane-bound enzymes, and inactivation of essential molecules located inside the cell. Other tests have shown that a large amount of fat in the diet can be a presumptive carcinogen. H. Hidaka et al., Effects of Fructooligosaccharides on Intestinal Flora and Human Health, 5 Bifidobacteria Microflora 37–50 (1986). Apart from these carcinogenic changes, still other injuries associated with free radicals include ulcerative diseases, inflammation, and ischemic bowel disease. Pectins and mannans prevent oxidative damage in various ways. They directly scavenge intestinal oxidants. Further, pectin can act as a chelating agent of loosely bound transition metals in the lumen. Moreover, pectin also reacts directly to prevent spontaneous dismutation of superoxide radicals and thus prevents the formation of hydrogen peroxide.

Still another dietary fiber according to the present invention is the pentosans (arabinoxylans). These plant fibers are composed predominantly of two pentoses, arabinose and xylose. Their molecular structure comprises a linear (1-4)-β-xylan backbone to which substituents are attached through O2 and O3 atoms of the xylosyl residues. Normally, arabinoxylans are insoluble, since they are bound to cell wall materials. The arabinoxylans that not bound to cell walls, however, can form highly viscous solutions, and they can absorb about ten times their weight of water. In the presence of oxidative agents, such as hydrogen peroxide/peroxidase, arabinoxylans can rapidly develop a gel network as a result of the re-establishment of cross-links.

Yet another dietary fiber that can be used in the present invention is the beta-glucans. The ubiquitous structural feature of these polysaccharides is well established. It consists of a linear chain of glucose units joined by both β-(1-3) and β-(104) linkages. These soluble gums are found in oats, barley, rice, and other cereal grains, and are known to have probiotic and cardiovascular benefits.

Still another dietary fiber that can be used in the present invention are arabinans and galactans, e.g. larch arabinogalactans. The arabinans are polymers of (1-5)-α-L-arabinose residues branched through O2, O3, or both, whereas the galactans are polymers of (1-4)-β-D-galactose residues. Galactans containing approximately 4% (1-6)-β-linkages, in addition to the usual β-(1-4) linkages, have also been found. The arabinogalactans occur in two distinct types. In grain legumes, the so-called Type I form is very common. The Type I form comprises polymers of β-(1-4)-galactan backbone substituted with arabinose side chains. The Type II arabinogalactan refers to the β-(1-3,6)-linked galactose polymers found in rapeseed cotyledon, which are also free of β-(1-4)-linked galactose residues. A low molecular weight arabinogalactan has been isolated from wheat flour, which was associated with a hydroxyproline-rich peptide.

As has been briefly discussed above, certain bacteria have also been shown to be beneficial to human gastrointestinal health. The intestinal flora of the human gut contains some $100 \times 10^9$ viable bacteria, representing 100 or more different species. The major bacteria can be roughly divided into three groups: (a) lactic acid bacteria, including lactobacilli, bifidobacteria, and streptococci; (b) anaerobic bacteria; and (c) aerobic bacteria Bacteria of the genus Lactobacillus have been used for several hundred years for treating various illnesses. Lactobacilli found in the human intestinal tract include *L. acidophilus, L. casei, L. fermentum, L. salivaroes, L. brevis, L. leichmannii, L. plantarum,* and *L. cellobiosus*. As discussed above, *L. acidophilus* has been shown to be exceptionally useful in treating conditions such as antibiotic-induced imbalances in the gastrointestinal microflora, hypercholesterolemia, vaginal infections, *E. coli* infection, oral contraceptive failure, depressed immunity, cancerous tumors, chronic granulomatous disease, and lactose indigestion. A. G. Shauss, Method of Action, Clinical Application, and Toxicity Data, 3 J. Advancement Med. 163 (1990). In vitro studies have shown *L. acidophilus* to have an inhibitory effect on the growth of pathogenic bacteria such as *Campylobacter pylori, Staphylococcus aureus, Pseudomonas aeruginosa,* and *Sarcina lutea* K. M. Shahani et al., Natural Antibiotic Activity of Lactobacillus Acidophilus and Bulgaricus, 11 Cultured Dairy Products J. 14 (1976). *L. acidophilus* can also reduce levels of toxic amines in the blood and may reduce the risk of developing colon cancer by inhibiting enzymes from fecal bacteria.

As has also been discussed above, bifidobacteria are also known to exert a beneficial influence on human health. These bacteria lower the intestinal pH, thereby inhibiting overgrowth of gastrointestinal pathogens. Therapeutic applications of bifidobacteria are indicated for the management of diarrhea and constipation, and the management of hepatic encephalopathy with hyperammonemia. Additional benefits include the production of B vitamins and breakdown of carcinogenic N-nitrosamines.

Bifidobacteria constitute the predominant microorganisms in the fecal flora of week-old breast-fed infants, making up 85–99% of the bacterial population. Upon weaning or upon the occurrence of perturbations, such an infection, vaccination, a sudden change in diet, and even the weather, can upset the balance of microorganisms in the gastrointestinal tract of these babies. Bifidobacteria can also be significantly reduced in elderly people due to a reduction of secreted gastric juices. The bifidobacterial population in adults is much more stable, however changes in diet, administration of antibiotics, exposure to gamma radiation or X-rays, disease, stress, and other disturbances can result in overgrowth of potentially pathogenic bacteria, decrease in beneficial bacteria (lactobacilli and bifidobacteria), and a resulting imbalance in the gastrointestinal flora. Hyperproliferation of harmful bacteria in the gut is associated with various forms of diarrhea, susceptibility to systemic infections, constipation, vague and acute abdominal symptoms, fatigue, dyspepsia, and presence of carcinogenic metabolites. Reestablishment of a normal balance of gastrointestinal flora can be accelerated, and such normal balance maintained, with dietary administration of lactobacilli and/or bifidobacteria.

Lactobacilli and bifidobacteria produce organic acids that reduce intestinal pH and thereby inhibit the growth of acid-sensitive undesirable bacteria. Lactobacilli produce lactic acid, hydrogen peroxide, and possibly acetic and benzoic acids. Bifidobacteria produce short chain fatty acids (SCFA) such as acetic, propionic, and butyric acids, as well as lactic and formic acids. The most plentiful short chain fatty acid produced by bifidobacteria is acetic acid, which has a wide range of antimicrobial activities against yeasts, molds, and other bacteria. Additionally, short chain fatty acids support normal gastrointestinal function by increasing colonic blood flow, stimulating pancreatic enzyme secretion, promoting sodium and water absorption, and potentiating intestinal mucosal growth. Bifidobacteria are also known to deconjugate bile salts to free bile acids, which are more inhibitory to susceptible bacteria than are the conjugated forms. Further, lactobacilli and bifidobacteria are able to produce other antimicrobial substances, such as bacteriocins, that inhibit the growth and proliferation of harmful bacteria in the gut.

Since the time of Hippocrates and throughout the Middle Ages, large doses of whey were prescribed by alchemists for treating many ailments, primarily acute septic conditions. Although it was not then known the reason that whey was useful for treating such conditions, recent studies have shown that whey contains antibodies or immunoglobulins capable of providing passive immunity against various pathogens and their toxic by-products. Antibodies or immunoglobulins are high molecular weight proteins produced in the bodies of mature animals that enhance immunity to infection by bacteria, viruses, fungi, protozoa, and the like. Antibodies in human and bovine milk promote development of a healthy gastrointestinal tract and provide protection against infections by pathogenic microorganisms. These antibodies interfere with the process that allows such pathogenic microorganisms to adhere to and colonize the intestinal lining. Studies have shown that immunoglobulins from whey are particularly effective against viruses (e.g., rotavirus), bacteria (e.g., *E. coli, Vibrio cholerae,* Salmonella), fungi (e.g., Candida), and protozoa (e.g., Cryptosporidium).

Detectable levels of anti-rotavirus antibodies ($IgG_1$) have been found in raw and pasteurized milk. R. H. Yolken, *Antibody to Human Rotavirus in Cow's Milk,* 312 New Eng. J. Med. 605 (1985). The high temperatures used in processing infant formula, however, destroy all traces of naturally occurring $IgG_1$. Many infants develop gastroenteritis around 6 months of age, about the time they are weaned from breast milk and started on formula.

Since infants and young children are highly susceptible to gastroenteritis, treatment of acute diarrhea with concentrated immunoglobulins has been investigated. In one study, infants hospitalized with acute rotavirus gastroenteritis were treated with an immunoglobulin concentrate derived from rotavirus-immunized cows. H. Hilpert et al., Use of Bovine Milk Concentrate containing Antibody to Rotavirus to Treat Rotavirus Gastroenteritis in Infants, 156 J. Infect. Dis. 158 (1987). These infants showed significantly reduced duration of rotavirus excretion. Thus, bovine milk immunoglobulins provided passive immunity against rotavirus gastroenteritis in human infants.

A bovine milk immunoglobulin concentrate derived from *E coli*-immunized cows has also been shown to inhibit colonization of enteropathic *E. coli* in affected infants. C. Mietens et al., Treatment of Infantile *E. Coli* Gastroenteritis with Specific Bovine Anti-*E. Coli* Milk Immunoglobulins, Eur. J. Pediatrics (1979). Stool samples showed a reduction in *E. coli* counts and the duration of diarrhea was shortened, demonstrating that this concentrate was effective in treating infantile diarrhea.

Inflammation of the gastrointestinal mucosa and diarrhea associated with Traveler's Diarrhea due to *E. coli* infection have been prevented by treatment with an immunoglobulin concentrate from bovine milk. C. Tacket et al., Protection by Milk Immunoglobulin Concentrate against Oral Challenge with Enterotoxigenic *Escherichia Coli,* 318 N. Engl. J. Med. 1240 (1988).

Immunoglobulins from bovine colostrum have been shown to be an effective treatment for diarrhea due to a pathogenic protozoan, Cryptosporidium. S. Tzipori et al., Remission of Diarrhea Due to Cryptosporidiosis in an Immunodeficient Child Treated with Hyperimmune Bovine Colostrum, 293 Br. Med. J. 1276 (1986). Immunodeficient individuals, particularly those with acquired immune deficiency syndrome (AIDS), are especially susceptible to Cryptosporidiosis.

Thus, immunoglobulin concentrates from milk contain immunologically active immunoglobulins that are capable of binding pathogenic microorganisms such as bacteria, viruses, fungi, and protozoa. Such immunoglobulin concentrates can be prepared from any starting material containing sufficient concentrations of immunologically active immunoglobulins, such as milk, whey, blood, and the like. An economically viable source of such immunoglobulins is the whey byproduct of the cheese making process. It has been estimated that approximately 85 million metric tons of whey are created annually as a byproduct of cheese production worldwide. About 34 million metric tons of whey are not economically utilized, and thus are discarded. The whey byproduct of cheese making, therefore, presents an inexpensive and ready source of immunoglobulins.

Numerous techniques are known to exist for producing dry concentrated protein extract from whey. This protein extract is commonly referred to as whey protein concentrate or "WPC." Such protein extraction and concentration techniques have been primarily concerned with preserving the food qualities of the WPC, such as taste, flavor, and solubility. Although these techniques are useful for producing food products, they almost universally destroy or substantially reduce the immunological activity of immunoglobulins in the concentrate by exposing the raw milk, whey, or protein concentrate to (1) excessive thermal (time and temperature) conditions, (2) excessive bacterial activity, or (3) excessive enzymes added in processing or resulting from bacterial activity.

Methods have been developed for separating immunologically active immunoglobulins from raw milk. U.S. Pat. Nos. 4,816,252 and 4,834,974 describe such methods, which are illustrative of methods that can be used for preparing an immunologically active immunoglobulin concentrate according to the present invention. Raw milk is first flash pasteurized to control microbial activity in the milk without significantly diminishing the immunological activity of the immunoglobulins in the milk. Next, the milk is exposed to an appropriate cheese starter culture, such as a lactobacillus, at carefully controlled temperatures and for limited times to achieve a selected degree of curd formation without significantly affecting the immunological activity of the immunoglobulins. The whey is then separated from the cheese curd and transferred to a clarifier or separator under carefully controlled conditions to remove fat and casein particles. The clarified whey is then subjected to ultrafiltration to remove or substantially reduce the amounts of small proteins, salts, and other non-protein materials in the retained protein concentrate or retentate. Ultrafiltration can be performed in stages to optimize purification of the immunoglobulins. Optionally, other concentration and purification steps, such as reverse osmosis and ion exchange chromatography, can then be used to further improve the purity and concentration of the immunoglobulin concentrate while maintaining the immunological activity thereof. The immunoglobulin concentrate is then dried through conventional freeze-drying or spray drying methods. The resulting dry immunoglobulin concentrate can then be stored at room temperature. At least about 7% of the total solids of immunoglobulin concentrates prepared by these methods comprise immunologically active immunoglobulins. When ultrafiltration and ion exchange chromatography are both used in the purification procedure, the proportion of immunologically active immunoglobulins as a percentage of total solids can be increased to at least about 50%. Repeated ion exchange chromatography steps can further increase the proportion of immunologically active immunoglobulins as a percentage of total solids. U.S. Pat. Nos. 4,816,252 and 4,834,974 are hereby incorporated herein by reference as illustrative of methods for purifying immunologically active immunoglobulin concentrate. The present invention is not limited to these methods, however, and any method of purifying and concentrating immunologically active immunoglobulins from milk, whey, or another suitable source is to be considered within the scope of the invention as long as an effective amount of immunologically active immunoglobulins is obtained in the "immunoglobulin composition." Bovine milk and bovine whey are preferred sources of immunoglobulins, but other species of animal could also be used.

In human and other animal tissues, peroxidases form part of a natural non-immune defense system and also play a role in protecting against microbial invasion of mucous membranes. Peroxidases occur in various exocrine gland secretions including salivary, lachrymal, bronchial, nasal, and intestinal secretions and in milk. Milk peroxidases, known as lactoperoxidases (LP) are the predominant enzymes in bovine milk. LP has no intrinsic antibacterial activity, however, together with hydrogen peroxide and thiocyanate anion it forms a potent natural antibacterial system, the so-called lactoperoxidase or LP system (for review see B. Reiter, Bacterial Inhibitors in Milk and Other Secretions with Special Reference to the Complement, Transferrin and Lactoperoxidase/Thiocyanate/Hydrogen Peroxide Systems, in Inhibition and Inactivation of Vegetative Microbes 31–60 (1976); B. Reiter & J.-P. Perraudin, Lactoperoxidase: Biological Functions, in 1 Peroxidases in Chemistry and Biology 143–180 (1991). The antibacterial effect of the LP system is mediated by the generation of short-lived oxidation products of thiocyanate anion (SCN), mainly the hypothiocyanate ion (OSCN). LP is a highly active enzyme, and very low concentrations are sufficient to establish an effective system. A wide range of bacterial species is affected by the LP system. Gram-negative bacteria generally are killed or their growth inhibited. Gram-positive bacteria usually are more resistant, however, and in general only their growth is inhibited. The LP system can also affect certain viruses, yeasts, and molds.

The thiocyanate anion is widely distributed in animal and human tissues, body-fluids, and secretions. It is found in the mammary, salivary, and thyroid glands, in the stomach and kidneys, in synovial, cerebral, and spinal fluid, and in lymph and plasma. The major dietary sources of thiocyanate ion are vegetables such as cabbage, cauliflower, and turnip, which are rich in glucosinolates that yield thiocyanate ion upon hydrolysis.

The activity of the LP system arises from an LP-catalyzed reaction in which hydrogen peroxide oxidizes thiocyanate ion (SCN) to form the hypothiocyanate ion (OSCN). The hypothiocyanate ion then oxidizes sulfhydryl groups in vital metabolic enzymes and other proteins of the microorganisms. The mechanisms of antimicrobial activity of the LP system result in damage to bacterial membranes and inhibition of essential transport mechanisms, such as those involving glucose and amino acids, and inhibition of synthesis of nucleic acids and proteins, including vital metabolic enzymes such as those involved in glycolysis.

Microorganisms inhibited by the LP system include a number of Gram-positive bacteria, including species of Staphylococcus and Streptococcus, and some Gram-negative species, e.g., *E. coli*, Salmonella, Pseudomonas. Some lactic acid bacteria, e.g. lactobacilli and bifidobacteria, are unaffected by the LP system because they contain a "reversal enzyme" called NAD(P)-OSCN-oxidase reductase, which prevents the antimicrobial activity of the LP system.

Lactoperoxidase is a highly active enzyme, and very low concentrations, along with low concentrations of hydrogen peroxide and thiocyanate ion, are sufficient to obtain an effective system. Hydrogen peroxide is known to be produced in many species of lactobacilli, and thiocyanate ion is widely distributed in animal and human tissues, body fluids, and secretions.

Advantages of the LP system include a greater antimicrobial efficacy and a wider spectrum of activity than existing preservatives. Also, the active antimicrobial agents of the LP system (OSCN and HOSCN) disappear from food after processing, thus providing a safe, long-lasting food preservative without the presence of the active preservative agents. Further, the LP system acts in synergy with other preservatives, thus increasing the efficacy of such other preservatives. Moreover, the LP system has a very low level of toxicity.

Lactoferrin is an iron-binding protein present in milk. For example, bovine milk contains about 200 mg/l of lactoferrin, and human milk and colostrum contain about 2–4 g/l and 6–8 g/l of lactoferrin, respectively. The affinity of lactoferrin for iron is very high, e.g. about 300 times that of the iron-transporting protein, transferrin, in blood plasma. A lactoferrin molecule binds one ferric ion ($Fe^{3+}$) by means of a bicarbonate-dependent reaction.

The high affinity for iron enables the use of lactoferrin for inhibiting iron-catalyzed processes, such as generation of free hydroxyl radicals, lipid peroxidation, and growth of microorganisms. Most microorganisms need iron for growth. Lactoferrin is able to inhibit the growth of such microorganisms by depriving them of iron. Lactoferrin is bacteriostatic to a wide range of microorganisms, including Gram-negative bacteria with a high iron requirement and some Gram-positive bacteria. Lactic acid bacteria, such as lactobacilli and bifidobacteria, have a low iron requirement and, in general, are not affected by lactoferrin. Although lactoferrin is primarily bacteriostatic, heat-treated lactoferrin is bactericidal. Heat-treated lactoferrin is easily obtained by heating lactoferrin at acidic pH.

Lactoferrin has been demonstrated in in vitro and in vivo tests to be effective against a variety of microorganisms, including *E. coli, Staphylococcus epidermidis, Streptococcus pneumoniae,* and *Candida albicans,* while at the same time promoting the growth of bifidobacteria. Lactoferrin retains iron at low pH and can pass through the acid environment of the stomach and enter the intestine unaltered.

As described above, various indigestible saccharides, such as FOS, have been developed for promoting the growth of bifidobacteria. Another substance that promotes the growth of bifidobacteria is gluconic acid and its salts (gluconates). It has been shown in in vitro fermentation tests that gluconate is utilized selectively by bifidobacteria as an energy source. H. Sato et al., Antioxidant Activity of Synovial Fluid, Hyaluronic Acid, and Two Subcomponents of Hyaluronic Acid, 31 Arthritis & Rheumatism (1988). In addition to promoting the growth of bifidobacteria, gluconic acid, like other organic acids, also suppresses the growth of certain harmful bacteria, such as *Clostridium perfringens.* Test results have further shown that ingested gluconic acid and gluconates are not absorbed in the small intestine, but instead are able to reach the large intestine where they can be utilized as an energy source by bifidobacteria. Sato et al., Antioxidant Activity of Synovial Fluid, Hyaluronic Acid, and Two Subcomponents of Hyaluronic Acid, 31 Arthritis & Rheumatism (1988).

In accordance with a preferred embodiment of the present invention, there is provided a bacteria- and fiber-containing composition for use as a dietary supplement. The formulation preferably includes a mixture of a beneficial human intestinal microorganism and a dietary fiber. Preferably, the dietary fiber is a member selected from the group consisting of pentosans, β-glucans, pectins and pectic polysaccharides, mannans, arabinans and galactans, and fructo-oligosaccharides, and mixtures thereof in optimal ratios to restore and maintain good gastrointestinal health.

In its most fundamental form, the bacteria- and fiber-containing formulations of the present invention include a mixture of effective amounts of a beneficial human intestinal microorganism and of dietary fiber. In a preferred embodiment, such beneficial human intestinal bacteria can be present in amounts preferably from about 0.1% to about 20% by weight, and more preferably about 5% to about 10% by weight. It is also preferred that the dietary fiber be present in amounts ranging from about 40% to about 60% by weight.

The beneficial human intestinal microorganism is preferably a member selected from the group consisting of lactobacilli and bifidobacteria. Preferred lactobacilli include *L. acidophilus, L. bulgaricus, L. casei, L. fermentum, L. salivaroes, L. brevis, L. leichmannii, L. plantarum,* and *L. cellobiosus*. *L. acidophilus* is more preferred and *L. acidophilus* strain NCFM is most preferred. Preferred bifidobacteria include *B. adolescentis, B. infantis, B. longum, B. thermophilum,* and *B. bifidum*. *B. adolescentis* is more preferred.

It is also preferable that the formulation contain an effective amount of an immunoglobulin composition comprising immunoglobulins that are immunologically active for binding antigens such as bacteria, viruses, fungi, and protozoa and the like. In preferred embodiments, such immunoglobulin composition is present in amounts ranging from about 40% to about 60% by weight.

It is also preferable that the formulation contain one or more additives for enhancing the activity of the body's non-immune defense system known as the LP system. Such additives can be added to the base formulation, with or without the presence of optional ingredients, in the following concentrations: lactoperoxidase in an amount in the range of about 0 to about 0.0300% by weight and thiocyanate salt in an amount in the range of about 0 to about 0.0500% by weight. Preferably, lactoperoxidase is present in an amount in the range of about 0.0001 to about 0.0300% by weight, and thiocyanate salt is present in an amount in the range of about 0.0001 to about 0.0500% by weight.

It is also preferable that the formulation contain additional optional ingredients for inhibiting the growth of harmful intestinal microorganisms and/or promoting the growth of beneficial human intestinal microorganisms, such as bifidobacteria. Such additives can be added to the base formulation, with or without the presence of other optional ingredients, in the following concentrations: lactoferrin in an amount in the range of about 0 to about 0.1000% by weight and gluconic acid, its nutritionally acceptable salts, or mixtures thereof in an amount in the range of about 0 to about 10% by weight. Preferably, lactoferrin is present in an amount in the range of about 0.0001 to about 0.1000% by weight, and gluconic acid, its nutritionally acceptable salts, or mixtures thereof in an amount in the range of about 0.1 to about 10% by weight.

The composition is preferably manufactured in powder form by agglomerating the dry, raw material ingredients in a suitable agglomerator so as to result in a finished product having a uniform composition with the precise proportions of the components. The bacteria are prepared, for example, by culturing in a rich medium such as LB, J. Miller, Experiments in Molecular Genetics, Cold Spring Harbor Laboratory, Cold Spring Harbor, N.Y. (1972), until the late log phase of growth is reached. The bacteria are then concentrated and lyophilized according to standard methods. The agglomerated material is then packaged in a suitable container. Just prior to consumption, the dry composition is reconstituted with water, juice, or the like to result in a smooth liquid composition that can be consumed orally. If desired, the composition can be formulated in liquid form. The preferred daily dosage of the formula ranges from about 5 to about 15 grams based on the powdered composition. The daily dosage can be ingested in a single serving or divided into various servings and taken at intervals. Preferably, the composition of the present invention is taken between meals.

The composition of the present invention can be used for maintaining gastrointestinal health as well as for treating diarrhea, constipation, and other types of gastrointestinal distress due to infection with pathogenic microorganisms such as *E. coli,* Salmonella, Candida, rotavirus, and Cryptosporidium by orally administering an effective amount of the composition. The effective amount will vary depending on the size and age of the individual, whether the selected effect is to maintain gastrointestinal health or to restore gastrointestinal health from distress due to infection with a pathogenic microorganism, the particular pathogenic microorganism involved, and the like. A person skilled in the art can routinely determine such an effective amount. The dry ingredients of the composition are stirred into water or juice, and the resulting suspension is taken by mouth. Preferably, dosage is in the range of about 20 to about 400 mg/kg of body weight. More preferably, dosage is in the range of about 70 to about 215 mg/kg of body weight. Doses of the bacteria and immunoglobulin-containing composition can be divided, wherein two or more administrations of divided doses are used to deliver a complete dose. Multiple doses can also be administered, but it is recommended that daily consumption be limited to 1 to 3 doses.

EXAMPLE

The following formulas represent specific embodiments of the invention. These embodiments may be prepared in the manner indicated above by blending together the stated raw ingredients in an agglomerator so as to result in a finished product having uniform composition with the precise proportions of the components as indicated. The agglomerated material is then packaged in a suitable container. In the preferred embodiment, the formula comprises the following ingredients stated in amounts by weight:

| Formulation A | |
|---|---|
| Inulin | 80% |
| *L. acidophilus* NCFM | 20% |
| Formulation B | |
| Inulin | 40% |
| Immunoglobulin comp. | 40% |
| *L. acidophilus* NCFM | 20% |

-continued

| | |
|---|---|
| Formulation C | |
| Pectin | 80% |
| L. acidophilus NCFM | 20% |
| Formulation D | |
| Guar Gum | 20% |
| Pectin | 30% |
| Immunoglobulin comp. | 40% |
| B. adolescentis | 10% |
| Formulation E | |
| Inulin | 30% |
| FOS | 15% |
| Immunoglobulin comp. | 49.72% |
| L. acidophilus NCFM | 2.5% |
| B. adolescentis | 2.5% |
| Lactoperoxidase | 0.03% |
| Sodium thiocyanate | 0.05% |
| Lactoferrin | 0.1% |
| Gluconic acid | 0.1% |
| Formulation F | |
| Inulin | 40% |
| Pectin | 9.98% |
| Immunoglobulin comp. | 40% |
| B. adolescentis | 10% |
| Lactoperoxidase | 0.02% |
| Formulation G | |
| Inulin | 10% |
| FOS | 10% |
| Pectin | 10% |
| Guar Gum | 10% |
| Immunoglobulin comp. | 52.95% |
| L. acidophilus NCFM | 7% |
| Potassium thiocyanate | 0.05% |
| Formulation H | |
| Inulin | 50.9% |
| Immunoglobulin comp. | 40% |
| B. adolescentis | 9% |
| Lactoferrin | 0.1% |
| Formulation I | |
| Inulin | 42% |
| Immunoglobulin comp. | 40% |
| B. adolescentis | 8% |
| Sodium gluconate | 10% |
| Formulation J | |
| Inulin | 20% |
| FOS | 20% |
| Pectin | 4.44% |
| Guar Gum | 1% |
| Immunoglobulin comp. | 40% |
| B. adolescentis | 10% |
| Lactoperoxidase | 0.01% |
| Ammonium thiocyanate | 0.05% |
| Sodium gluconate | 4.5% |
| Formulation K | |
| FOS | 36% |
| Pectin | 3.5% |
| Guar Gum | 2.5% |
| Immunoglobulin comp. | 42% |
| L. acidophilus NCFM | 10% |
| Lactoferrin | 0.01% |
| Gluconic acid | 5.99% |
| Formulation L | |
| Inulin | 40% |
| Immunoglobulin comp. | 40% |
| B. adolescentis | 10% |
| Lactoperoxidase | 0.0001% |
| Sodium thiocyanate | 0.0001% |
| Lactoferrin | 0.0001% |
| Gluconic acid | 10% |

-continued

| | |
|---|---|
| Formulation M | |
| Inulin | 70% |
| Pentosans | 10% |
| L. acidophilus NCFM | 20% |
| Formulation N | |
| Inulin | 60% |
| β-glucans | 20% |
| L. acidophilus NCFM | 20% |
| Formulation O | |
| Inulin | 50% |
| Arabinogalactans | 30% |
| L. acidophilus NCFM | 20% |

The disclosures of the following related applications are hereby incorporated herein by reference: Ser. No. 08/674,115, filed Jul. 1, 1996, now U.S. Pat. No. 5,744,134; Ser. No. 08/437,316, filed May 9, 1995, now U.S. Pat. No. 5,531,989; and Ser. No. 08/331,140, filed Oct. 28, 1994, now U.S. Pat. No. 5,531,988.

We claim:

1. A bacteria- and fiber-containing composition for promoting gastrointestinal health comprising:
   (a) an effective amount of beneficial human intestinal microorganisms; and
   (b) an effective amount of dietary fiber.

2. The composition of claim 1 wherein said dietary fiber is a member selected from the group consisting of pentosans, β-glucans, pectins and pectic polysaccharides, mannans, arabinans and galactans, fructo-oligosaccharides, and mixtures thereof.

3. The composition of claim 2 wherein said mannans are members selected from the group consisting of guar gum, locust bean gum, konjac, xanthan gum, and mixtures thereof.

4. The composition of claim 2 wherein said arabinans and galactans are larch arabinogalactans.

5. The composition of claim 2 wherein said fructo-oligosaccharides are selected from the group consisting of inulin, soy fructo-oligosaccharides, banana fiber, and mixtures thereof.

6. The composition of claim 1 wherein said beneficial human intestinal microorganisms are selected from the group consisting of lactobacilli, bifidobacteria, and mixtures thereof.

7. The composition of claim 6 wherein said beneficial human intestinal microorganisms are lactobacilli.

8. The composition of claim 7 wherein said lactobacilli are selected from the group consisting of *Lactobacillus acidophilus, Lactobacillus bulgaricus, Lactobacillus casei, Lactobacillus fermentum, Lactobacillus salivaroes, Lactobacillus brevis, Lactobacillus leichmannii, Lactobacillus plantarum, Lactobacillus cellobiosus,* and mixtures thereof.

9. The composition of claim 8 wherein said lactobacilli are *Lactobacillus acidophilus*.

10. The composition of claim 9 wherein said *Lactobacillus acidophilus* is strain NCFM.

11. The composition of claim 6 wherein said beneficial human intestinal microorganisms are bifidobacteria.

12. The composition of claim 11 wherein said bifidobacteria are selected from the group consisting of *Bifidobacterium adolescentis, Bifidobacterium infantis, Bifidobacterium longum, Bifidobacterium thermophilum, Bifidobacterium bifdum,* and mixtures thereof.

13. The composition of claim 12 wherein said bifidobacteria are *Bifidobacterium adolescentis*.

14. The composition of claim 1 further comprising an effective amount of an immunoglobulin composition comprising concentrated immunologically active immunoglobulins.

15. The composition of claim 14 wherein said immunoglobulin composition further comprises a carrier.

16. The composition of claim 15 wherein said carrier comprises at least one member selected from the group consisting of a carbohydrate and a lipid, wherein said carbohydrate is capable of being an energy source for said beneficial human intestinal microorganism and said lipid aids in reconstitution of said immunoglobulin composition.

17. The composition of claim 16 wherein said carbohydrate comprises maltodextrin and said lipid comprises lecithin.

18. The composition of claim 17 wherein said immunoglobulin composition is purified from a source selected from the group consisting of milk, milk products, and whey.

19. The composition of claim 18 wherein said source is bovine.

20. The composition of claim 14 wherein the effective amount of the beneficial human intestinal microorganisms is about 0.1% to about 20% by weight, the effective amount of soluble dietary fiber is about 40% to about 60% by weight, and the effective amount of immunoglobulin composition is about 40% to about 60% by weight.

21. The composition of claim 1 further comprising about 0.0001% to about 0.1000% of lactoferrin and about 0 to about 10% by weight of a member selected from the group consisting of gluconic acid, its nutritionally acceptable salts, and mixtures thereof.

22. The composition of claim 14 further comprising about 0.0001% to about 0.1000% of lactoferrin and about 0 to about 10% by weight of a member selected from the group consisting of gluconic acid, its nutritionally acceptable salts, and mixtures thereof.

23. The composition of claim 22 comprising about 0.1% to about 10% by weight of a member selected from the group consisting of gluconic acid, its nutritionally acceptable salts, and mixtures thereof.

24. The composition of claim 1 further comprising about 0.0001% to about 0.0500% by weight of thiocyanate salt and about 0 to about 0.0300% by weight of lactoperoxidase.

25. The composition of claim 14 further comprising about 0.0001% to about 0.0500% by weight of thiocyanate salt and about 0 to about 0.0300% by weight of lactoperoxidase.

26. The composition of claim 21 further comprising about 0.0001% to about 0.0500% by weight of thiocyanate salt and about 0 to about 0.0300% by weight of lactoperoxidase.

27. The composition of claim 22 further comprising about 0.0001% to about 0.0500% by weight of thiocyanate salt and about 0 to about 0.0300% by weight of lactoperoxidase.

28. The composition of claim 23 further comprising about 0.0001% to about 0.0500% by weight of thiocyanate salt and about 0 to about 0.0300% by weight of lactoperoxidase.

29. The composition of claim 28 comprising about 0.0001% to about 0.0300% by weight of lactoperoxidase.

30. A method of restoring and maintaining gastrointestinal health comprising the step of orally administering a bacteria- and fiber-containing composition comprising:
(a) an effective amount of beneficial human intestinal microorganisms; and
(b) an effective amount of dietary fiber.

31. The method of claim 30 wherein said dietary fiber is a member selected from the group consisting of pentosans, β-glucans, pectins and pectic polysaccharides, mannans, arabinans and galactans, fructo-oligosaccharides, and mixtures thereof.

32. The method of claim 31 wherein said mannans are members selected from the group consisting of guar gum, locust bean gum, konjac, xanthan gum, and mixtures thereof.

33. The method of claim 31 wherein said arabinans and galactans are larch arabinogalactans.

34. The method of claim 31 wherein said fructo-oligosaccharides are selected from the group consisting of inulin, soy fructo-oligosaccharides, banana fiber, and mixtures thereof.

35. The method of claim 30 wherein said beneficial human intestinal microorganisms are selected from the group consisting of lactobacilli, bifidobacteria, and mixtures thereof.

36. The method of claim 35 wherein said beneficial human intestinal microorganisms are lactobacilli.

37. The method of claim 36 wherein said lactobacilli are selected from the group consisting of *Lactobacillus acidophilus, Lactobacillus bulgaricus, Lactobacillus casei, Lactobacillus fermentum, Lactobacillus salivaroes, Lactobacillus brevis, Lactobacillus leichmannii, Lactobacillus plantarum, Lactobacillus cellobiosus,* and mixtures thereof.

38. The method of claim 37 wherein said lactobacilli are *Lactobacillus acidophilus.*

39. The method of claim 38 wherein said *Lactobacillus acidophilus* is strain NCFM.

40. The method of claim 35 wherein said beneficial human intestinal microorganisms are bifidobacteria.

41. The method of claim 40 wherein said bifidobacteria are selected from the group consisting of *Bifidobacterium adolescentis, Bifidobacterium infantis, Bifidobacterium longum, Bifidobacterium thermophilum, Bifidobacterium bifidum,* and mixtures thereof.

42. The method of claim 41 wherein said bifidobacteria are *Bifidobacterium adolescentis.*

43. The method of claim 30 further comprising an effective amount of an immunoglobulin composition comprising concentrated immunologically active immunoglobulins.

44. The method of claim 43 wherein said immunoglobulin composition further comprises a carrier.

45. The method of claim 44 wherein said carrier comprises at least one member selected from the group consisting of a carbohydrate and a lipid, wherein said carbohydrate is capable of being an energy source for said beneficial human intestinal microorganism and said lipid aids in reconstitution of said immunoglobulin composition.

46. The method of claim 45 wherein said carbohydrate comprises maltodextrin and said lipid comprises lecithin.

47. The method of claim 46 wherein said immunoglobulin composition is purified from a source selected from the group consisting of milk, milk products, and whey.

48. The method of claim 47 wherein said source is bovine.

49. The method of claim 43 wherein the effective amount of the beneficial human intestinal microorganism is about 0.1% to about 20% by weight, the effective amount of soluble dietary fiber is about 40% to about 60% by weight, and the effective amount of immunoglobulin composition is about 40% to about 60% by weight.

50. The method of claim 30 further comprising about 0.0001% to about 0.1000% of lactoferrin and about 0 to about 10% by weight of a member selected from the group consisting of gluconic acid, its nutritionally acceptable salts, and mixtures thereof.

51. The method of claim 43 further comprising about 0.0001% to about 0.1000% of lactoferrin and about 0 to about 10% by weight of a member selected from the group consisting of gluconic acid, its nutritionally acceptable salts, and mixtures thereof.

52. The method of claim 51 comprising about 0.1% to about 10% by weight of a member selected from the group consisting of gluconic acid, its nutritionally acceptable salts, and mixtures thereof.

53. The method of claim 30 further comprising about 0.0001% to about 0.0500% by weight of thiocyanate salt and about 0 about 0.0300% by weight of lactoperoxidase.

54. The method of claim 43 further comprising about 0.0001% to about 0.0500% by weight of thiocyanate salt and about 0 to about 0.0300% by weight of lactoperoxidase.

55. The method of claim 50 further comprising about 0.0001to about 0.0500% by weight of thiocyanate salt and about 0 to about 0.0300% by weight of lactoperoxidase.

56. The method of claim 51 further comprising about 0.0001% to about 0.0500% by weight of thiocyanate salt and about 0 to about 0.0300% by weight of lactoperoxidase.

57. The method of claim 52 further comprising about 0.0001% to about 0.0500% by weight of thiocyanate salt and about 0 to about 0.0300% by weight of lactoperoxidase.

58. The method of claim 57 comprising about 0.0001% to about 0.0300% by weight of lactoperoxidase.

59. The method of claim 30 wherein said step of orally administering said bacteria- and fiber-containing composition modulates infection by a pathogenic microorganism that results in gastrointestinal stress.

60. The method of claim 59 wherein said pathogenic microorganism is selected from the group consisting of bacteria, viruses, fungi, and protozoa.

* * * * *